United States Patent [19]
Nakao et al.

[11] Patent Number: 5,195,967
[45] Date of Patent: Mar. 23, 1993

[54] ANTICLOTTING DEVICE AND METHOD FOR USE WITH IV CATHETERS

[76] Inventors: Naomi L. Nakao, 303 E. 57th St., New York, N.Y. 10022; Peter J. Wilk, 185 West End Ave., New York, N.Y. 10023

[21] Appl. No.: 836,768

[22] Filed: Feb. 18, 1992

[51] Int. Cl.⁵ ............................................. A61M 5/00
[52] U.S. Cl. ......................................... 604/83; 604/84
[58] Field of Search ................... 604/6, 4, 65, 67, 80, 604/81, 82–86, 89–92; 128/DIG. 12

[56] References Cited

U.S. PATENT DOCUMENTS

| | | | |
|---|---|---|---|
| 3,916,892 | 11/1975 | Latham, Jr. | 604/83 |
| 3,965,896 | 6/1976 | Swank | 604/28 |
| 4,444,198 | 4/1984 | Petre | 604/30 |
| 4,464,172 | 8/1984 | Lichtenstein | 604/65 |
| 4,493,693 | 1/1985 | Bilstad et al. | 604/6 |
| 4,534,764 | 8/1985 | Mittleman et al. | 604/90 |
| 4,538,918 | 9/1985 | Mittleman | 604/85 |
| 4,540,406 | 9/1985 | Miles | 604/4 |
| 4,553,958 | 11/1985 | LeCocq | 604/67 |
| 4,769,001 | 9/1988 | Prince | 604/67 |

Primary Examiner—Stephen C. Pellegrino
Assistant Examiner—Ralph Lewis
Attorney, Agent, or Firm—R. Neil Sudol; Henry D. Coleman

[57] ABSTRACT

A method for use in an intravenous tube assembly comprises the steps of automatically monitoring liquid flow along a fluid flow path extending through an intravenous catheter to detect at least a partial cessation of flow along the fluid flow path and, upon detecting a diminution of liquid flow along the fluid flow path, automatically feeding an anticlotting agent to the fluid flow path. An assembly, for implementing the method takes the form of a pressure sensing device operatively connected to the catheter for automatically detecting at least a partial cessation of liquid flow along a fluid flow path extending through the catheter. The assembly also includes a feeder mechanism operatively connected to the catheter and the sensing device for automatically feeding an anticlotting agent to the fluid flow path through the catheter upon a detection by the sensing device of a diminution of liquid flow along the fluid flow path and, more particularly, of intravenous liquid flow in a distal direction into a patient's circulatory system.

19 Claims, 2 Drawing Sheets

ANTICLOTTING DEVICE AND METHOD FOR USE WITH IV CATHETERS

BACKGROUND OF THE INVENTION

This invention relates to a technique and a related device for preventing the formation of blood clots in intravenous catheters.

In an intravenous feeding assembly, an intravenous catheter is inserted into a person's vein and connected at a proximal end to an intravenous tube extending from a liquid supply. Frequently, intravenous lines are lost because the monitoring personnel forget to change the infusion bag and a clot forms in the catheter. In patients who have accessible veins, the intravenous line has to be restarted by a physician or a nurse specialist. Precious moments can be lost while the physician or nurse specialist is being sought. During that time, the patient does not receive intravenous fluid and does not have an intravenous line.

In addition, there are a large number of cases in which no further veins are accessible. In such cases, another intravenous can be started only with great difficulty, for example, by having a surgeon cut down into a vein. In this group of patients, the maintenance of an intravenous line is especially crucial.

Intravenous lines are particularly critical for certain kinds of patients. For example, after a myocardial infarction, a patient's myocardium is irritable and the patient can go into a life-threatening arrythmia such as ventricular fibrillation. During that time, if there is no available intravenous port, intravenous medication cannot be injected and the patient dies. Also, when the patient is in ventricular fibrillation, it is extremely difficult to obtain venous access because blood is not being efficiently pumped. The absence of an intravenous line in the patient at that time can be a direct cause of death.

Patients who are bleeding and are receiving blood represent another critical group. When the intravenous line becomes clotted and the line is lost, it is again difficult to obtain venous access. Such a patient can bleed to death or exanguinate, if there is no readily available intravenous line.

Another critical group is patients who have a severe, life-threatening infection requiring the continuous or continual supply of antibiotics. In such cases, where the intravenous line is clotted and a physician or nurse specialist cannot be found, the patient can die.

In yet another critical group, the patients have a pulmonary embolus and require continuous heparinization. In such a patient, a clot in an intravenous line causing an interruption in the heparin flow of only a few minutes can result in the formation of another pulmonary embolism and instantaneous death.

Other consequences of interruption of intravenous lines include the prodding, bruising and pricking of unfortunate patients. For old people, especially, the restarting of intravenous lines is a constant source of pain and suffering.

Heparin is an anticlotting compound and is provided in catheters which are inserted intravenously for enabling periodic access to a patient's blood or circulatory system. Inasmuch as such catheters are closed at a proximal end, for example, by a self-sealing polymeric membrane, the heparin remains in the catheter owing to suction forces. Such a device is known as a heparin lock.

OBJECTS OF THE INVENTION

An object of the present invention is to provide a method for reducing the incidence of blood clots forming in intravenous catheters.

Another object of the present invention is to provide an associated device for reducing the incidence of blood clots forming in intravenous catheters.

Another, more particular, object of the present invention is to provide an automatic anticlotting device, such as an automatic heparin lock. A further particular object of the present invention is to provide a device for automatically sensing a diminution of liquid flow through an intravenous catheter and for automatically introducing heparin into the catheter upon detection of a diminution of liquid flow termination.

SUMMARY OF THE INVENTION

A method for use in an intravenous tube assembly comprises, in accordance with the present invention, the steps of automatically monitoring liquid flow along a fluid flow path extending through an intravenous catheter to detect at least a partial cessation of flow along the fluid flow path and, upon detecting a diminution of liquid flow along the fluid flow path, automatically feeding an anticlotting agent to the fluid flow path.

Pursuant to another feature of the present invention, the method further comprises the step of automatically blocking communication between the catheter and an intravenous tube connected to the catheter.

According to another feature of the present invention, the step of automatically feeding comprises the step of automatically feeding a predetermined aliquot of the anticlotting agent to the fluid flow path. The anticlotting agent may be fed in via injection.

Alternatively, a cessation of liquid flow through the fluid flow path is detected by automatically sensing a change in pressure, particularly a drop in pressure, along the fluid flow path extending through the catheter. The drop in pressure may be sensed by a an assembly which exerts a pressure, e.g., via a swingable door or valve member, against the fluid in the flow path. When the presure in the flow path drops below a predetermined value, the door or valve opens, thereby allowing the anticlotting agent to flow from a storage chamber into the flow path.

An associated assembly for use with an intravenous catheter comprises, in accordance with the present invention, a sensor device operatively connected to the catheter for automatically detecting at least a partial cessation of liquid flow along a fluid flow path extending through the catheter and further comprises a feeder mechanism operatively connected to the catheter and the sensor device for automatically feeding an anticlotting agent to the fluid flow path through the catheter upon a detection by the sensor device of a diminution of liquid flow along the fluid flow path and, more particularly, of intravenous liquid flow in a distal direction into a patient's circulatory system.

Pursuant to another feature of the present invention, the assembly for automatically feeding an anticlotting agent to a catheter or to an intravenous path extending through the catheter also comprises a body member which is connected to the catheter and which carries the sensor device and the feeder mechanism. Thus, an assembly in accordance with the present invention advantageously comprises a modular article which is connectable to the proximal end of a conventional catheter, downstream of an intravenous feed tube. The assembly for automatically feeding an anticlotting agent to a catheter or to an intravenous path extending through the catheter may alternatively comprise a distal end of an intravenous tube.

In accordance with an additional feature of the present invention, a closure device is operatively connected to the catheter and the sensor device for automatically blocking communication between the catheter and an intravenous tube connected to the catheter. The closure device operates to block communication upon a cessation or diminution of liquid flow through the catheter.

Closing or blocking communication between the catheter and an intravenous feed tube may be partially implemented by a one-way valve on the body member. The one-way valve permits liquid flow through the body member into the catheter and prevents liquid flow in a reverse direction.

Pursuant to another feature of the present invention, the feeder mechanism includes means for automatically injecting a predetermined aliquot of the anticlotting agent to the catheter.

As an alternative to a pressure detection mechanism, the sensor device may automatically sense the presence of air or oxygen along the fluid flow path extending through the catheter. The anticlotting agent used in the present invention is preferably heparin.

A device for use with an intravenous catheter comprises, in accordance with another conceptualization of the present invention, a pressure sensor operatively connected to the catheter for automatically detecting a diminution of liquid pressure along a fluid flow path extending through the catheter. A feeder mechanism is operatively connected to the catheter and the sensor for automatically feeding an anticlotting agent to the fluid flow path upon a detection by the sensor of a diminution in liquid pressure the fluid flow path.

According to another feature of the present invention, the device further comprises a body member defining a channel in turn defining a part of the fluid flow path. The body member encloses a chamber containing a predetermined amount of the anticlotting agent. The sensor includes a door or valve member movably connected to the body member and disposed between the channel and the chamber.

Pursuant to a more particular feature of the present invention, the device further comprises means for exerting pressure on the anticlotting agent in the chamber. That pressure exerting component may take the form of a spring or a balloon.

Use of a device in accordance with the present invention serves to reduce the incidence of blood clots forming in intravenous catheters. In particular, a device in accordance with the present invention prevents a clot from forming in an intravenous catheter upon the exhausting of an intravenous liquid supply, whether saline solution, blood plasma or other liquid.

DETAILED DESCRIPTION

Figure 1:
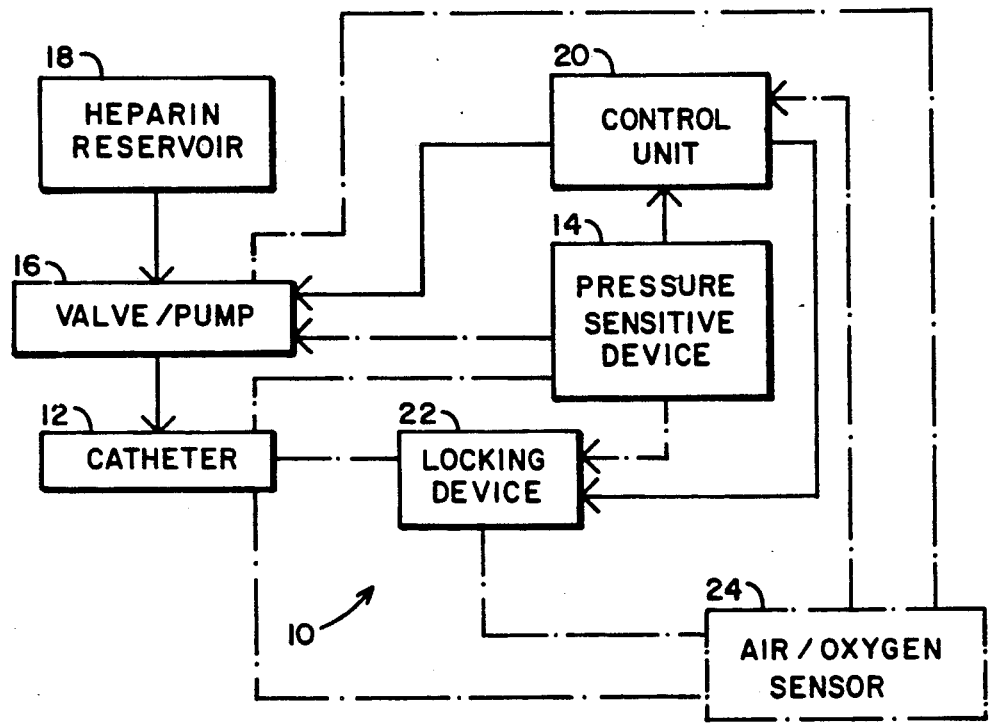
FIG. 1 is a block diagram of an electrically or mechanically implemented automatic heparin lock in accordance with the present invention.

As illustrated in FIG. 1, an automatic heparin lock device or assembly 10 connectable to a catheter 12 comprises a pressure sensitive device 14 operatively connected to the catheter for acting in response to fluid pressure along an intravenous path extending from a liquid supply (not shown) through the catheter. More particularly, pressure sensitive device 14 detects, or is responsive to, a drop in pressure which occurs upon a termination of a liquid stream along the fluid path. The liquid stream is replaced by air, which results in a pressure drop.

As further illustrated in FIG. 1, heparin lock or assembly 10 also comprises a valve or pump 16 which is disposed between a heparin reservoir 18, on the one hand, and catheter 12 or the fluid path including through the catheter, on the other hand. Valve or pump 16 is operated by pressure sensitive device 14 either directly or via a control unit or logic circuit 20. Upon a detection by pressure sensitive device 14 of a pressure drop concomitant with a diminution of intravenous liquid flow through catheter 12, valve or pump 16 is actuated to feed heparin from reservoir 18 to catheter 12 or, equivalently, to the intravenous path extending through the catheter.

Heparin lock or assembly 10 additionally comprises a locking device or mechanism 22 which functions to block communication between catheter 12 and an intravenous tube connected thereto. Locking device 22 is operatively connected to pressure sensitive device 14 for operating in conjunction therewith or in response to signals transmitted directly from pressure sensitive device 14 or indirectly therefrom via control unit 20.

As an alternative to pressure sensitive device 14, an air or oxygen sensor 24 may be operatively connected to valve 16, either directly or via control unit 20, and to catheter 12. Upon detecting air or, more specifically, oxygen in catheter 12 or the fluid path extending through the catheter, sensor 24 acts to actuate valve 16 to transfer heparin from reservoir 18 to the intravenous path extending through catheter 12.

Figure 2:
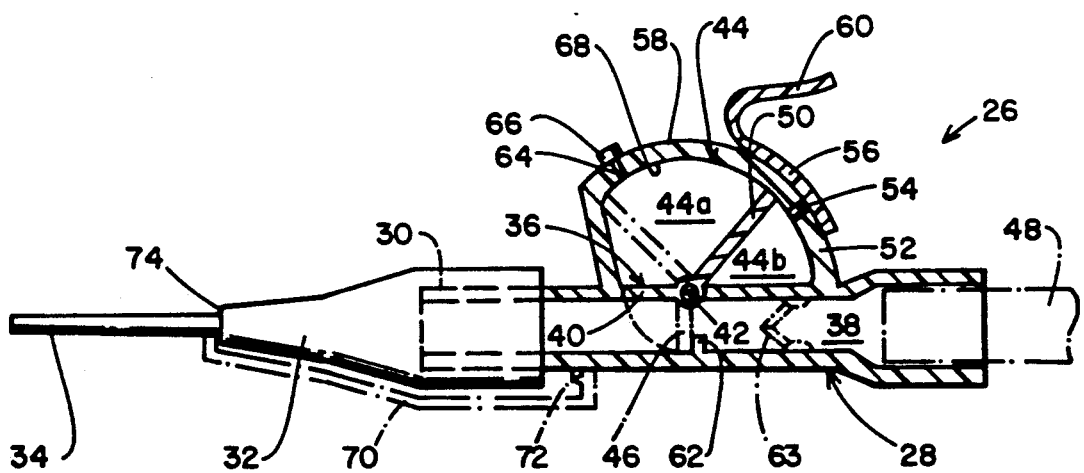
FIG. 2 is a schematic cross-sectional longitudinal view of a mechanical heparin lock in accordance with the present invention.

As illustrated in FIG. 2, a mechanically implemented automatic heparin lock 26 includes a body member 28 having a distal end 30 insertable into the proximal end of a catheter body or holder 32, thereby connecting the heparin lock 26 to a catheter 34. Body member 28 includes a pressure monitoring or detecting device 36 which senses or is responsive to a diminution or partial cessation of liquid flow through a main channel 38 of body member 28. Channel 38 defines a fluid flow path which extends through catheter 34 and catheter body 32 in a distal direction into a patient's circulator system (not illustrated).

Pressure monitoring device 36 includes a door or valve element 40 rotatably hinged to body member 28 at a pivot pin 42. In a pre-use configuration, door 40 closes an ancillary chamber 44 in body member 28 and thereby prevents communication between that chamber and channel 38. Upon an actuation of pressure monitoring device 36, in response to a drop in fluid pressure in channel 38, door 40 rotates in a counter-clockwise direction about pivot pin 42 to a blocking position illustrated in dot-dash lines at 46. In blocking position 46, door 40 extends transversely across channel 38 and serves to block communication between catheter body 32 and catheter 34, on the one hand, and an intravenous tube 48, on the other hand. Tube 48 is connected to catheter 34 via heparin lock member 28 prior to the commencement of an intravenous feeding or transfer operation.

Heparin lock 26 further comprises a rotary piston element 50 which is rigid with door 40 and rotatably attached to body member 28 via pivot pin 42. Rotary piston element 50 is disposed in chamber 44 and partitions that chamber into a first portion 44a and a second portion 44b. First chamber portion 44a contains a predetermined aliquot of an anticlotting agent such as heparin (not illustrated), while second chamber 44b serves in the maintenance of a suction hold on piston element 50 prior to installation of heparin lock 26, i.e., prior to a coupling of body member 28 to catheter body 32 and intravenous tube 48 and an initiation of liquid flow along a fluid flow path extending through intravenous tube 48, channel 38 of body member 26, and catheter 34. To that end, a wall 52 of main body 28 is provided with an aperture 54 extending to second chamber portion 44b.

Prior to utilization of heparin lock 26 in conjunction with intravenous catheter 34, a closure strip 56 is adhesively attached to an outer surface 58 of wall 52 to close aperture 54 and thereby maintain a suction force on piston element 50 which prevents the rotation of that element and concomitantly door 40 about pin 42 and locks the aliquot of heparin in first chamber portion 44a. Closure strip 56 is provided with a pull tab 60 by which a user removes the strip form outer surface 58 and thereby opens aperture 54 upon a connection of intravenous tube 48 and body member 28 to catheter body 32 and a commencement of a liquid flow along a fluid flow path extending through the intravenous tube, channel 38 of body member 26, and catheter 34.

During a flow of intravenous liquid along the feed path through intravenous tube 48, channel 38 of body member 26, and catheter 34, the fluid pressure in channel 38 pushes against door 40, keeping the door closed and the heparin charge contained in chamber portion 44a. Upon a pressure drop in channel 38, which corresponds to a diminution of intravenous liquid flow, door 40 is pushed open and into blocking position 46 by the heparin in chamber portion 44a and by rotary piston 50. To facilitate this rotation of door 40 and the feed or injection of the heparin charge from chamber portion 44a into channel 38 and towards catheter 34, pressure monitoring device 36 may be provided with a spring element (not shown) which tends to rotate door 40 towards blocking position 46. Of course, the rotary force exerted by this biasing spring is not so great as to open door 40 and discharge the heparin while intravenous liquid is flowing through channel 38 of body member 26. It is to be noted that the biasing spring functions, together with door 40, as a sensor or detector of fluid pressure in channel 38. The biasing spring additionally functions with door 40 to block communication between catheter 34 and intravenous tube 48, upon a detection of a drop in pressure signaling a partial cessation or diminution of liquid flow through channel 38. The biasing spring cooperates with rotary piston element 50 to feed or inject a heparin charge into channel 38 and accordingly into the fluid flow path extending to catheter 34.

Body member 28 is provided along channel 38 with a stop 62 which arrests the counterclockwise motion of door 40 and piston element 50 and defines the channel blocking position 46 of door 40. In addition, body member 28 may be provided along channel 38 with a one-way valve 63 which together with door 40 serves to prevent a back-flow of heparin into tube 48.

Body member 28 may also be provided with a bore 64 extending through wall 52 to chamber portion 44a for enabling the loading of a heparin charge into that chamber portion. Bore 64 is closed or sealed by a plug 66.

During a feeding of heparin from chamber portion 44a to channel 38 by piston element 50, an outer end of that element moves in a sealing engagement against a correspondingly profiled inner surface 68 of wall 52.

Heparin lock body member 28 may be provided with an optional latch 70 pivotably mounted to body member 28 at 72 for swinging around catheter body 32 to engage a distal end 74 thereof in a releasable snap lock fit. Latch 70 serves to prevent or inhibit an untimely disengagement of body member 28 and catheter body 32.

Figure 3:
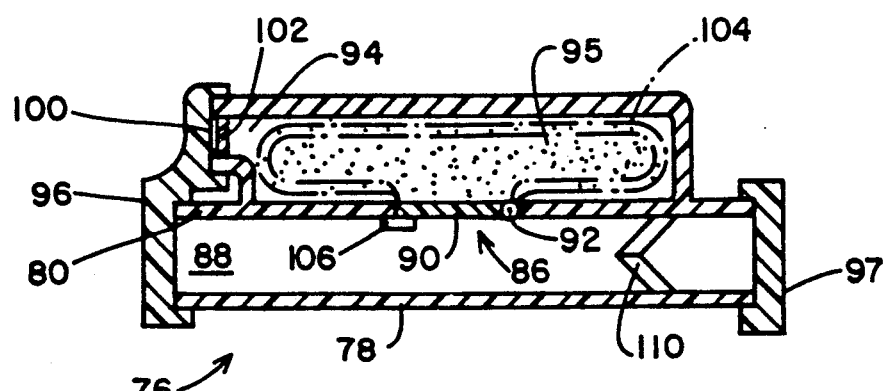
FIG. 3 is a schematic cross-sectional longitudinal view of another mechanical heparin lock in accordance with the present invention.

As illustrated in FIG. 3, a mechanically implemented automatic heparin lock 76 includes a body member 78 having a distal end 80 insertable into the proximal end of a catheter body or holder 82 (FIGS. 4A-4D), thereby connecting the heparin lock 76 to a catheter (not shown). Body member 78 includes a pressure monitoring or detecting device 86 which senses or is responsive to a diminution or partial cessation of liquid flow through a main channel 88 of body member 78. Channel 88 defines a fluid flow path which extends through the catheter and catheter body 82 in a distal direction into a patient's circulatory system (not illustrated).

Pressure monitoring device 86 includes a door or valve element 90 rotatably hinged to body member 78 at a pivot pin 92. In a pre-use configuration, door 90 closes an ancillary chamber 94 in body member 78 and thereby prevents communication between that chamber and channel 88. Upon an actuation of pressure monitoring device 86, in response to a drop in fluid pressure in channel 88, door 90 rotates in a counter-clockwise direction about pivot pin 92 enable the flow of an aliquot of heparin 95 from chamber 94 into channel 88.

Heparin lock 76 further comprises a pair of end caps 96 and 97 disposed on opposite ends of body member 78 to close channel 88 and thereby maintain the channel in a sterile condition. Prior to the commencement of an intravenous feeding or transfer operation, end caps 96 and 97 are removed and an intravenous tube 98 (FIGS. 4A-4D) connected to catheter 84 via heparin lock member 78, as illustrated in FIG. 4A.

The removal of end cap 96 simultaneously opens a breather aperture 100 which may be provided with a semipermeable membrane 102 which permits the passage of air but not a liquid such as heparin. Alternatively or additionally, a balloon 104 is provided inside chamber 94 for containing the heparin and pressing it through door 90 upon a falling of the fluid pressure in channel 88 below a predetermined threshold value. Breather membrane 102 and balloon 104 each serve as a barrier which prevent the leakage or flow of heparin out through breather aperture 100.

Prior to use of heparin lock 76, door 90 is held closed by a glue layer or spot 106 of a water-dispersible material such as sugar. Consequently, neither pressure due to balloon 104 nor the internal pressure of the heparin, released upon a removal of end cap 96 and an opening of breather aperture 100, will result in an immediate opening of door 90 and a flow of heparin from chamber 94 into channel 88.

Figure 4A:
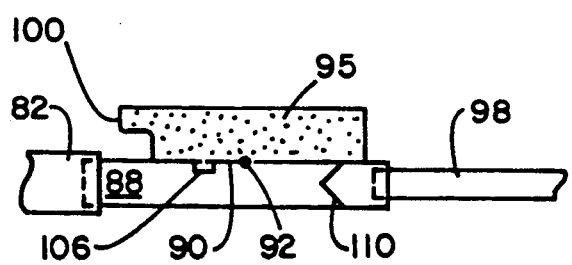
FIGS. 4A-4D are schematic cross-sectional views showing different stages in the utilization and operation of the automatic heparin lock of FIG. 3.
Figure 4B:
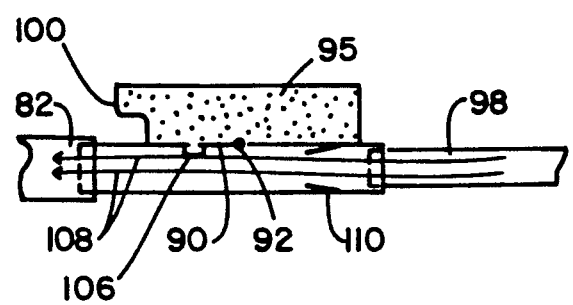
Figure 4C:
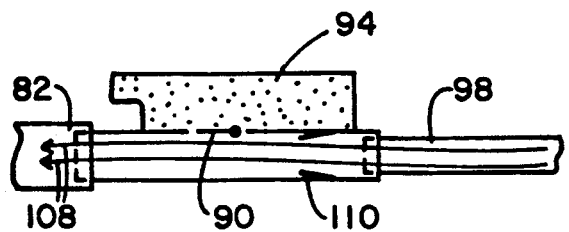
Figure 4D:
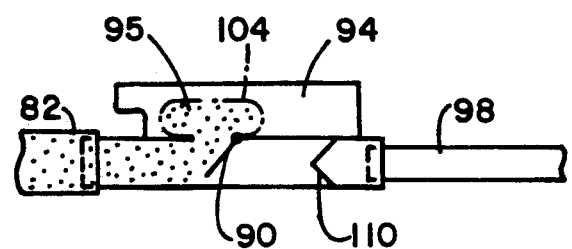

FIG. 4A shows heparin lock 76 after a removal of end caps 96 and 97 and a connection of intravenous tube 98 and catheter body 82 to the heparin lock body member 78, while FIG. 4B shows the heparin lock 76 just after intravenous fluid has begun to flow through channel 88, as indicated by flow arrows 108. After a period of time determined largely by the composition of the water dispersible or dissolvable material of layer or spot 106, that layer or spot disappears, as shown in FIG. 4C. Subsequently, during a continued flow of intravenous liquid along the feed path through intravenous tube 98, channel 88 of body member 76, and catheter body 82, the fluid pressure in channel 88 pushes against door 90, keeping the door closed and the heparin charge contained in chamber 94. Later, upon a pressure drop in channel 88, corresponding to a diminution of intravenous liquid flow, door 90 is pushed outwardly into channel 88 (FIG. 4D) by the heparin in chamber 94 and, additionally or alternatively, by balloon 104.

To further facilitate this rotation of door 90 and the feed or injection of the heparin charge from chamber 94 into channel 88 and towards catheter/catheter body 82, pressure monitoring device 86 may be provided with a spring element (not shown) which tends to rotate door 90 in the counterclockwise direction, as illustrated in the drawing. The rotary force exerted by this biasing spring, by the pressure of the heparin and/or by balloon 104, is not so great as to open door 90 and discharge the heparin while intravenous liquid is flowing through channel 88 of body member 76.

Body member 78 may be provided along channel 88 with a one-way valve 110 which together with door 90 serves to prevent a back-flow of heparin into tube 98.

It is to be noted that heparin injected or fed into an intravenous fluid flow path during operation of an automatic heparin lock in accordance with the present invention is held or maintained in the fluid flow path in the region of the catheter, thereby preventing the catheter from clogging with clotted blood. The heparin is held in the fluid flow path, without entering the patient, by virtue of the same forces acting in a conventional heparin lock.

Although the invention has been described in terms of particular embodiments and applications, one of ordinary skill in the art, in light of this teaching, can generate additional embodiments and modifications without departing from the spirit of or exceeding the scope of the claimed invention. For example, the geometry of the heparin containing chamber can take different forms, apparent to those skilled in the art. A plurality of heparin chambers may be connected via respective doors or valves to the channel in the body member.

Accordingly, it is to be understood that the drawings and descriptions herein are proferred by way of example to facilitate comprehension of the invention and should not be construed to limit the scope thereof.

What is claimed is:

1. A method for use in an intravenous tube assembly, comprising the steps of:

automatically monitoring liquid flow along a fluid flow path extending through an intravenous catheter to detect at least a partial cessation of liquid flow along said fluid flow path;

upon detecting at least a partial cessation of liquid flow along said fluid flow path, automatically feeding an anticlotting agent to said fluid flow path; and upon feeding of said anticlotting agent to said fluid flow path, maintaining said anticlotting agent within a predetermined region of said fluid flow path.

2. The method defined in claim 1 wherein said step of maintaining includes the step of automatically blocking communication between said catheter and an intravenous tube connected to said catheter.

3. The method defined in claim 1 wherein said step of automatically feeding comprises the step of automatically feeding a predetermined aliquot of said anticlotting agent to said fluid flow path.

4. The method defined in claim 1 wherein said step of automatically feeding includes the step of automatically injecting said anticlotting agent into said fluid flow path.

5. The method defined in claim 1 wherein said step of monitoring includes the step of automatically sensing a change in pressure along said fluid flow path.

6. The method defined in claim 1 wherein said anticlotting agent is heparin.

7. A device for use with an intravenous catheter, comprising:

sensor means adapted to be connected to the catheter for automatically detecting at least a partial cessation of liquid flow along a fluid flow path extending through the catheter;

feeder means adapted to be connected to the catheter and operatively connected to said sensor means for automatically feeding an anticlotting agent to said fluid flow path upon a detection by said sensor means of at least a partial cessation of liquid flow along said fluid flow path; and holding means adapted to be connected to the catheter and connected to said feeder means for maintaining said anticlotting agent within a predetermined region of said fluid flow path upon feeding of said anticlotting agent to said fluid flow path by said feeder means.

8. The device defined in claim 7, further comprising a body member defining a channel in turn defining a part of said fluid flow path, said sensor means, said feeder means and said holding means being mounted to said body member, said body member being attachable to the catheter so that said channel communicates with the catheter, said feeder means including in said body member a chamber containing a predetermined amount of said anticlotting agent, said feeder means further including a door movably connected to said body member and disposed between said channel and said chamber, said anticlotting agent being fed to said fluid flow path upon an opening of said door.

9. The device defined in claim 8, further comprising means for exerting pressure on said anticlotting agent in said chamber.

10. The device defined in claim 7, further comprising a body member adapted to be connected to the catheter and carrying said sensor means and said feeder means, said body member being formed with a channel for defining a portion of said fluid flow path and for communicating with the catheter upon an attachment of said body member to the catheter.

11. The device defined in claim 10, further comprising a one-way valve in said body member, said one-way valve permitting liquid flow through said body member into said catheter along said fluid flow path and preventing liquid flow in a reverse direction.

12. The device defined in claim 7 wherein the sensor means includes means for automatically sensing a change in pressure along said fluid flow path.

13. The device defined in claim 7 wherein said holding means includes closure means adapted to be connected to the catheter and operatively connected to said sensor means for automatically blocking liquid flow along said fluid flow path and from said catheter upon a detection by said sensor means of at least a partial cessation of liquid flow along said fluid flow path.

14. The device defined in claim 7 wherein said feeder means includes means for automatically feeding a predetermined aliquot of said anticlotting agent into said fluid flow path.

15. The device defined in claim 7 wherein said anticlotting agent is heparin.

16. A device for use with an intravenous catheter, comprising:
   sensor means adapted to be connected to the catheter for automatically detecting a diminution of liquid pressure along a fluid flow path extending through the catheter;
   feeder means adapted to be connected to the catheter and said sensor means for automatically feeding an anticlotting agent to said fluid flow path upon a detection by said sensor means of a diminution in liquid pressure said fluid flow path; and
   holding means adapted to be connected to the catheter and operatively connected to said feeder means for maintaining said anticlotting agent within a predetermined region of said fluid flow path, upon feeding of said anticlotting agent to said fluid flow path by said feeder means.

17. The device defined in claim 16, further comprising a body member defining a channel in turn defining a part of said fluid flow path, said sensor means, said feeder means and holding means being mounted to said body member, said body member being attachable to the catheter so that said channel communicates with the catheter, said feeder means including in said body member a chamber containing a predetermined amount of said anticlotting agent, said feeder means further including a door movably connected to said body member and disposed between said channel and said chamber, said anticlotting agent being fed to said fluid flow path upon an opening of said door.

18. The device defined in claim 17, further comprising means for exerting pressure on said anticlotting agent in said chamber, said means for exerting pressure being attached to said body member and in at least partial contact with said anticlotting agent in said chamber.

19. The device defined in claim 18 wherein said means for exerting includes a balloon attached to said body member and disposed inside said chamber, said balloon containing said anticlotting agent.

* * * * *